United States Patent [19]

Anderson et al.

[11] Patent Number: Plant 6,884

[45] Date of Patent: Jun. 27, 1989

[54] CHRYSANTHEMUM PLANT-DAY NEUTRAL

[75] Inventors: Neil O. Anderson; Peter D. Ascher; Richard E. Widmer, all of St. Paul, Minn.

[73] Assignee: Regents of the University of Minnesota, Minneapolis, Minn.

[21] Appl. No.: 197,801

[22] Filed: May 23, 1988

[51] Int. Cl.[4] ..... A01H 5/00

[52] U.S. Cl. ..... Plt./77

[58] Field of Search ..... Plt./77

[56] References Cited

PUBLICATIONS

M. Okada, "Studies on Flower Bud Differentiation and Flowering in Chrysanthemums", 1963.

1988–89 Chrysanthemum Manual of Gloeckner, pp. 70–71.

Yoder Brothers, Inc. Catalog, p. 4, 28, 47–50, 1983.

R. E. Widmer, "Garden Chrysanthemums", Publication of University of Minnesota Agricultural Extension Service AG–FS–1121, Rev. 1983.

*Primary Examiner*—Robert E. Bagwill

*Attorney, Agent, or Firm*—Merchant, Gould, Smith, Edell, Welter & Schmidt

[57] ABSTRACT

A Chrysanthemum plant having flat capitulum form; composite, semi-double decorative flowers; creamy white ray florets; height of approximately 27 cm. in a four inch greenhouse plant and approximately 20.8 cm. as an outdoor garden plant; uniform three week photoperiodic flowering response to short days; being day neutral and insensitive to heat delay and capable of flowering year around under any photoperiodic conditions.

3 Drawing Sheets

BACKGROUND INFORMATION

The present invention comprises a new and distinct cultivar of *Dendranthema grandiflora* (*Chrysanthemum morifolium* Ramat.), identified as MN Sel. 83-267-3.

MN Sel. 83-267-3 is a product of a planned breeding program which had the objective of creating chrysanthemum inbreds to increase homozygosity at loci controlling important phenotypic traits and for eventual use as a parent in creating F1 hybrid seed chrysanthemums. The plant originated as a seedling from a self-pollination of MN Sel. 79-214-2 (unnamed and unpatented), made in 1982 at St. Paul, Minn., during the course of breeding efforts in an on-going garden chrysanthemum breeding project. MN Sel. 83-267-3 is a second generation inbred.

MN Sel. 83-267-3 was discovered and selected as one flowering plant within the progeny of the stated cross in the fall of 1983, in the St. Paul campus field test plots at the University of Minnesota. The first act of asexual reproduction of MN Sel. 83-267-3 was accomplished when vegetative cuttings were taken in March–April 1984, in a controlled environment in St. Paul, Minn., from the initial selection that had been dug from the field in October 1983. MN Sel. 83-267-3 has been maintained as part of the breeding germplasm for crossing objectives.

In 1987, MN Sel. 83-267-3 was selected to be included in five environments (Chart A) for evaluation as a day neutral (DN) plant. It was established to be a three week short day (SD) response group plant. Under increasingly stringent long day (LD) photoperiods, it was superior to standard greenhouse and garden SD cultivars, as well as garden DN cultivars. Other characteristics that made this plant outstanding were the semidouble decorative flower type, short plant height, and insensitivity to thermophotoperiodic delay in flower bud initiation and development. The distinctive characteristics caused us to select the plant for further testing for production as a greenhouse pot plant.

MN Sel. 83-267-3 has not been observed under all possible environmental conditions. The phenotype may vary significantly with variations in environment such as temperature, light intensity and day length. Under normal growing conditions that satisfy the factors for plant growth, the normal phenotype occurs. However, we have observed that when grown during December through February, with low light levels, the flower color will be uniformly purple under any of the following conditions: 1. 62° F. nights (N), SD photoperiod (0800–1600 hours); 2. 62° F. N, LD photoperiod: natural daylength plus four-hour night interruption (NI) with incandescent light (2200–0200 hours); 3. 62° F. N, LD photoperiod: natural daylength conditions plus 18 hours 400 watt HID-HPS light (0300–2100 hours) and 4. 55° F. N, LD photoperiod: natural daylength plus four-hour NI with incandescent light (2200–0200 hours). These purple flower changes are not sports due to mutation. Descriptions of these changes are included as appropriate. Horticultural examination of selected units initiated since 1983 have demonstrated that the combination of characteristics as herein described for MN Sel. 83-267-3 are firmly fixed and are retained through successive generations of asexual reproduction.

Day Neutrality

Chrysanthemums are quantitative short day (SD) plants for flower bud initiation (FBI) and qualitative (obligate) SD plants for flower bud development (FBD) (Schwabe, 1952). If a SD plant is grown under photoperiods exceeding the 13.5 hour (average) critical SD photoperiod, it will not flower (e.g. continue with FBD after FBI). FBD of SD chrysanthemums is reversibly controlled by red and far-red light. Continuous or intermittent lighting, using either incandescent (red and far-red light) or fluorescent (red light) lights, in the middle of each long dark period (night) inhibits FBI and FBD in SD cyrysanthemums (Cathey and Borthwick, 1970).

All SD chrysanthemums eventually initiate terminal flower buds (i.e. undergo autonomous FBI) under long day (LD) conditions (Langton, 1977). They will not, however, continue with FBD under LD conditions unless they are day neutral (DN). True DN plants are rare. In a DN plant, FBD is not inhibited by LD photoperiods and will continue (following autonomous FBI) for all flower buds (primaries, secondaries, tertiaries, etc.) under any photoperiodic conditions, e.g. SD or any LD (in which the duration of light is longer than the critical SD photoperiod), and with any combination of light quality (red, far-red, red/far-red).

Cathey, H. M. and H. A. Borthwick, 1970. Photoreactions controlling flowering of *Chrysanthemum morifolium* (Ramat. and Hemsl.) illuminated with fluorescent lamps. Plant Physiology 45:235–239.

Langton, F. A. 1977. The response of early-flowering chrysanthemums to daylength. Scientia Horticulturae 7:277–289.

Schwabe, W. W. 1952. Effects of temperature, daylength, and light intensity in the control of flowering in the chrysanthemum. Report of the 13th International Horticultural Congress 2:952–960.

Potential Impact of Day Neutral/Heat Insensitive Cultivars

Day neutral (DN) and heat delay insensitive cultivars could impact greenhouse chrysanthemum production in several ways. Cultivars insensitive to heat delay have already proved useful to the commercial grower, allowing for scheduling of such cultivars under any high temperatures normally incurred in greenhouse production schedules (30°–39° C.) When this trait is coupled with day neutrality, thermophotoperiodic interactions (heat buildup under black cloth used for short day photoperiods) are eliminated, allowing for production in the wide range of temperatures and photoperiods inherent with seasonal and latitudinal changes. Genotypes such as Mn. Sel. 83-267-3 should be adaptable to a wider latitudinal and seasonal production range than currently available heat-delay insensitive cultivars which are not DN.

Since a DN cultivar will flower under any photoperiod, there is no need for chrysanthemum growers to manipulate the environment to induce flowering. Manual or automated photoperiodic black cloth, used to induce short days for flowering, would become unnecessary and/or obsolete. This would eliminate the costs of initial investments in the black cloth system, maintenance and depreciation, as well as the labor involved in operating the system twice daily. In addition, the commercial production protocols of 2–3 weeks of long days for vegetative growth, followed by 8+ weeks of short days for flower bud initiation and development would be unnecessary. A DN cultivar does not need to be moved into long and then short day photoperiods for flowering. Rather, such cultivars could be flowered under naturally long daylengths (spring to fall) and supplemental long day lighting could be added during winter months (low light conditions and short day photoperiods) or they could be flowered using current production schedules until growers phase out investments in existing black cloth systems.

DESCRIPTION OF THE DRAWINGS

This new chrysanthemum plant is illustrated by the accompanying photographic drawings.

DESCRIPTION OF THE NEW PLANT

Figure 1:
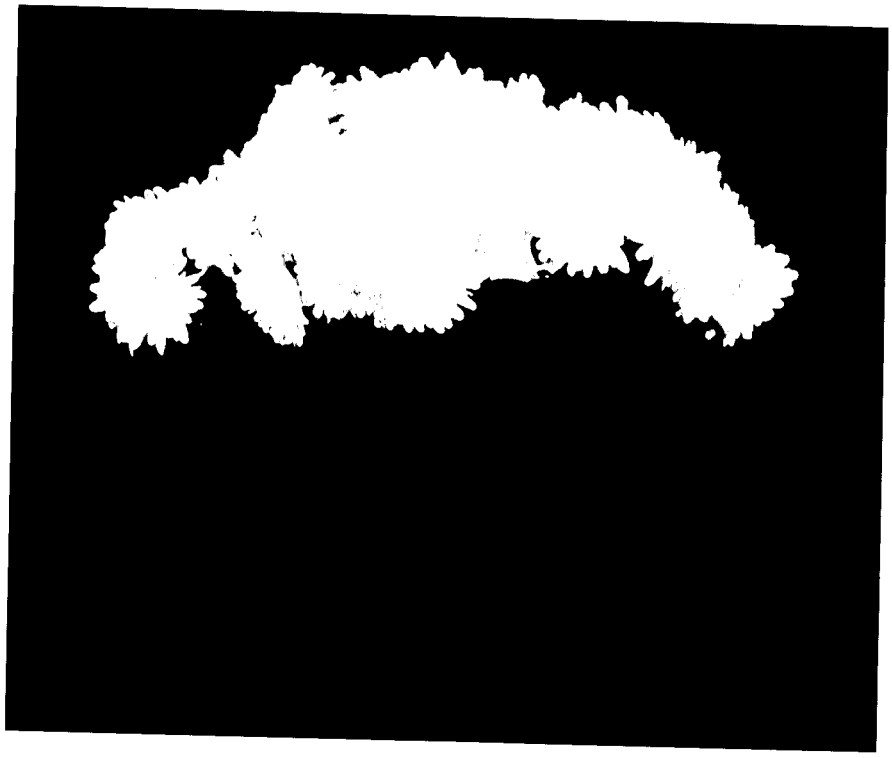
FIG. 1 is a photographic print in full color showing a four-inch potted plant in full bloom, the colors shown being as nearly true as it is reasonably possible to obtain by conventional photographic procedures. All photographs of this cultivar were taken from plants grown at St. Paul, Minn., and flowered in February, 1988.
Figure 2:
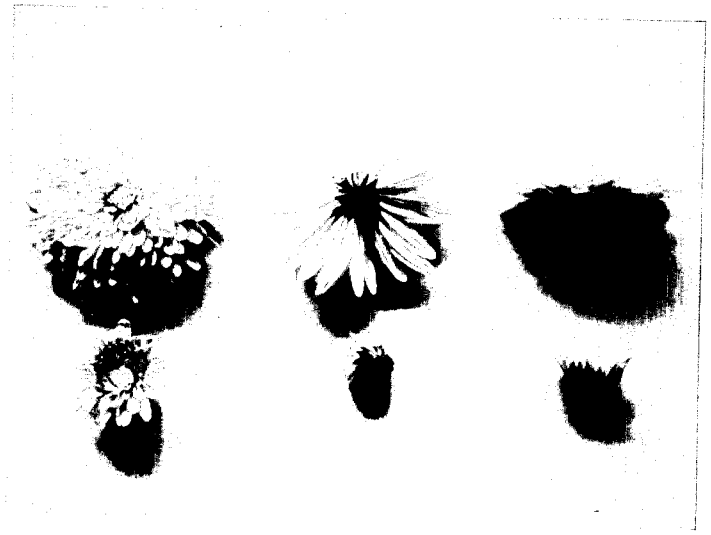
FIG. 2 is a black and white photograph of three views of the inflorescence of MN Sel. 83-267-3.
Figure 3:
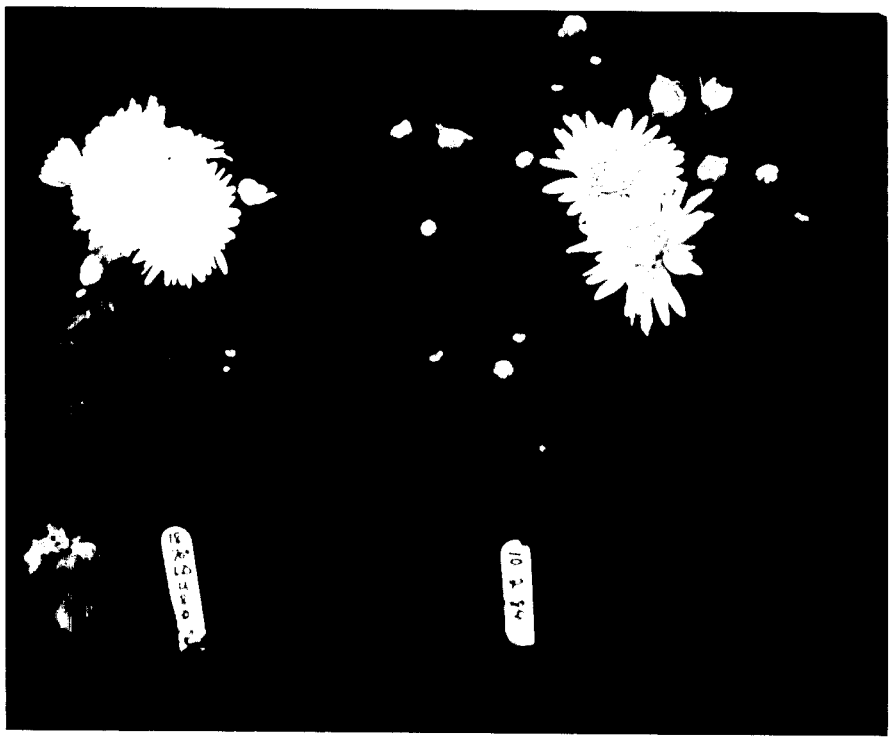
FIG. 3 is a color photograph of four-inch potted plants in full bloom with the normal (left) and purple (right) flower color that appear under the stated conditions.
Figure 4:
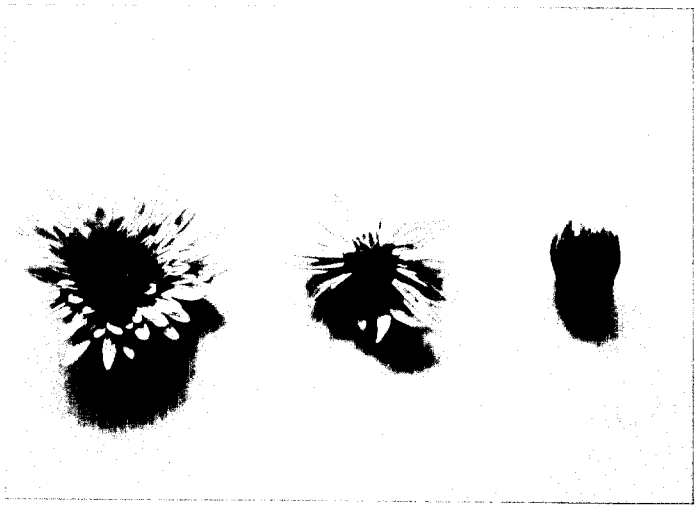
FIG. 4 is a black and white photograph of three views of the inflorescence with purple flower color.
Figure 5:
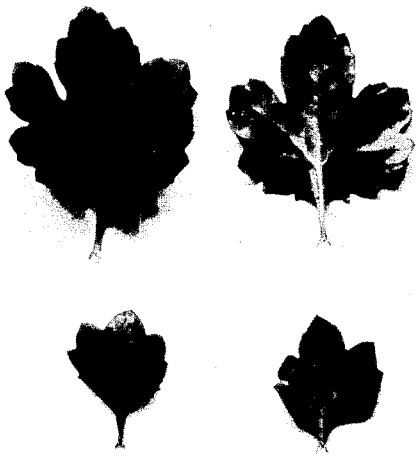
FIG. 5 shows the leaves of MN Sel. 83-267-3 at two stages of maturity.

The following traits have been repeatedly observed and are determined to be basic characteristics of MN Sel. 83-267-3 which, in combination, distinguish this chrysanthemum as a new and distinct cultivar. The color designations were made using the R.H.S. Colour Chart published by The Royal Horticultural Society, London, England (copyright 1938) between 1000 and 1100 hours on Feb. 18, 1988, in a glass greenhouse under full-sun on a cloudless day at St. Paul, Minn. (45° N latitude).

THE PLANT

Origin: Seedling.

Parentage:

*Seed parent.*—MN Sel. 79-214-2 (unnamed and unpatented).

*Pollen parent.*—MN Sel. 79-214-2 (unnamed and unpatented).

Classification:

*Botanic.*—*Dendranthema grandiflora* (*Chrysanthemum morifolium*).

*Commercial.*—Greenhouse pot plant and outdoor garden plant.

Form: Perennial, herbaceous bush.

Height:

*As a four-inch pot plant.*—About 27 cm.

*As an outdoor garden plant.*—About 20.8 cm.

Growth: Terminal, with a spreading habit, moderate sturdiness and strength.

Branching: Under natural conditions.

Foliage: Quantity — abundant, with 11–15 leaves per 9–24 cm of stem.

Leaves:

*Color.*—Upper side — Parsley Green 962/0. Under side — Spinach Green 960/4.

*Shape.*—Lanceolate, lobed and serrated.

*Venation.*—Pinnately veined.

*Surface texture.*—Upper side — Glabrous. Under side — Finely hirsute to glabrous.

*Size.*—About 6.9 cm long×7.1 cm wide.

Petioles: About 2.4 cm.

THE BUD

Form: Elliptical.

Size:

*Diameter.*—About 0.7 cm.

*Depth.*—About 0.4 cm.

Opening: The bud opens slowly.

Color:

*When phyllaries first divide.*—Spinach Green 960/2.

*When florets begin to unfurl.*—Spinach Green 960/3.

Phyllaries: The outside of the receptacle bears many phyllaries as involucral bracts.

*Form.*—Spear-shaped and flat.

*Color.*—Inside surface — Spinach Green 960/3. Outside surface — Spinach Green 962/0.

*Surface texture.*—Slightly pubescent.

Peduncle:

*Length.*—About 0.8 cm.

*Surface texture.*—Pubescent.

*Strength.*—Terminal erect and strong. Laterals weaker and bending to a 45° angle.

*Color.*—Spinach Green 960/3.

THE FLOWER

Blooming capability: This plant is day neutral and insensitive to heat delay. It can be flowered the year around under any photoperiodic conditions.

*Short day response.*—Three to five weeks.

*Long day response.*—Night interrupted lighting — Five to 13 weeks, depending on light quality and temperature (Chart A). 24-hour constant lighting — Five to six weeks.

*Recommended flowering.*—March 1 to December 1.

*Natural flowering seasons.*—About September 20 to October to October 10.

Inflorescence:

(1. *Capitulum.*—Form. — Flat capitulum when first open, becoming semihemispherical at maturity.

*Flower type.*—Composite, semi-double decorative.

*Size.*—About 8.3 cm. diameter across the face.

2. *Corolla of Ray Florets.*—Color (general tonality from a distance of three meters). — Creamy white. Color:

| | | |
|---|---|---|
| Immature: Outer (upper) | Naples Yellow 403/3 | Cyclamen Purple |
| (reverse) | Naples Yellow 403/3 | Fuchsia 30/2 Purple 28/3 |
| Inner (upper) | Canary Yellow 2/3 | Erythrite Red oo27/3 |
| (reverse) | Canary Yellow 2/3 | Erythrite Red oo27/2 |
| Mature: Outer (upper) | White | Rhodamine Purple 29/3 |
| (reverse) | White | Fuchsia Purple 28/3 |
| Inner (upper) | Naples Yellow 403/3 | Rhodamine Purple 29/3 |
| (reverse) | Naples Yellow 403/3 | Mallow Purple 630/3 |

3. *Corolla of Disc Florets.*—Color (immature). — Lemon Yellow 4/2. Color (mature). — Lemon Yellow 4/1.

REPRODUCTIVE ORGANS

Androecium: Present in disc florets only.

*Pollen color.*—Indian Yellow 6/1.

*Stamens.*—Five. Syngenesiously arranged.

*Filament length.*—About 2 mm.

Gynoecium: Present in disc and ray florets.

*Ovary.*—Inferior, monolocular, with one anatropous and tenuinucellate (single layer of epidermal cells) ovule. Single integument.

*Size.*—About 0.57 mm length×0.21 m width.

*Embryo sac.*—Tetrasporic, Asterad type.

*Pistil.*—One per disc floret and one per ray floret.

*Disc floret style length.*—About 1.5 mm.

*Ray floret style length.*—About 1.7 mm.

*Stigma color.*—Disc and ray florets — Lemon Yellow 4/2.

*Style color.*—Disc and ray florets — Lemon Yellow 4/1.

The day neutrality and insensitivity to thermophotoperiodic delay in flowering of the cultivar of this invention is illustrated by the evaluation of the plants in the various diverse environments detailed in the following chart:

CHART A

COMPARISON OF MN SEL. 83-267-3 AND MINNWHITE

| Environment | Mean No. of Days to Flower First | Mean No. of Days to Flower Third | Mean No. of Leaves to Terminal Flower Bud (Long day Leaf No.) | Mean Stem Length | Mean No. of Strap-Shaped Leaves |
|---|---|---|---|---|---|
| MN SEL. 83-267-3 | | | | | |
| 1[z] | 21.8 | 27.3 | 15.0 | 18.5 | 1.3 |
| 2 | 47.5 | 56.5 | 15.8 | 24.0 | 1.5 |
| 3 | 37.4 | 50.5 | 13.5 | 23.8 | 3.0 |
| 4 | 87.5 | 89.0 | 16.0 | 20.8 | 1.5 |
| 5 | 39.8 | 48.3 | 11.3 | 9.0 | 3.5 |
| MINNWHITE | | | | | |
| 1 | 45.8 | 36.5 | 20.3 | 16.6 | 3.5 |
| 2 | 53.5 | 89.5 | 23.5 | 20.1 | 5.5 |
| 3 | — | — | 13.8 | 11.6 | 9.0 |
| 4 | — | — | 13.8 | 7.5 | 5.5 |

1[z] SD, 62° F. nights, January–April 1987.

2 LD red light inght interruption (2200–0200 hours), 62° F. nights, January–April 1987.

3 LD far-red night interruption (2200–0200 hours), 80° F. nights, June–August, 1987.

4 LD red and far-red day continuation and pre-dawn (St. Paul field), 63° F. nights, July–October, 1987.

5 LD red and far-red light (24 hours continuous), 83° F. constant, September–November 1987.

We claim:

1. A new and distinct cultivar of *Chrysanthemum morifolium,* Ramat., as shown and described, and particularly characterized as to novelty by the combined characteristics of day neutrality, a semidouble decorative flower type, short plant height, and insensitivity to thermophotoperiodic delay in flower bud initiation and development.

* * * * *

UNITED STATES PATENT AND TRADEMARK OFFICE

CERTIFICATE OF CORRECTION

PATENT NO. : Plant 6,884

DATED : June 27, 1989

INVENTOR(S) : Anderson, et al

It is certified that error appears in the above-identified patent and that said Letters Patent is hereby corrected as shown below:

Col. 2, line 38
"cyrysanthemums" should be --chrysanthemums--

Col. 5, line 28
delete "October to"

Signed and Sealed this

Twenty-sixth Day of June, 1990

*Attest:*

HARRY F. MANBECK, JR.

*Attesting Officer*

*Commissioner of Patents and Trademarks*